(12) United States Patent
Hashimoto et al.

(10) Patent No.: US 8,927,234 B2
(45) Date of Patent: Jan. 6, 2015

(54) METHOD FOR PRODUCING HYALURONIC ACID

(75) Inventors: Masamichi Hashimoto, Machida (JP); Teruaki Kakema, Machida (JP); Kenji Fujii, Machida (JP); Masahisa Ikemi, Machida (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 831 days.

(21) Appl. No.: 13/055,628

(22) PCT Filed: Jul. 25, 2008

(86) PCT No.: PCT/JP2008/063427
§ 371 (c)(1),
(2), (4) Date: May 5, 2011

(87) PCT Pub. No.: WO2010/010631
PCT Pub. Date: Jan. 28, 2010

(65) Prior Publication Data
US 2011/0207178 A1  Aug. 25, 2011

(51) Int. Cl.
*C12P 19/26* (2006.01)
*C08B 37/00* (2006.01)
*C08B 37/08* (2006.01)

(52) U.S. Cl.
CPC ............. *C12P 19/26* (2013.01); *C08B 37/0003* (2013.01); *C08B 37/0072* (2013.01)
USPC .......................... 435/84; 435/252.31; 435/200

(58) Field of Classification Search
CPC ...................................... C12P 19/26
USPC ......................................... 435/84
See application file for complete search history.

(56) References Cited

U.S. PATENT DOCUMENTS 5,316,926 A * 5/1994 Brown et al. ................ 435/101

FOREIGN PATENT DOCUMENTS

JP  07-046992  *  2/1995  ............. C12P 19/26

OTHER PUBLICATIONS

JP07-46992 machine translation.*
Armstrong et al, Culture conditions affect the mlelcular weight properties of hyaluronic acid produced by *Streptococcus zooepidemicus*, Applied and Environmental Microbiology, 1997, vol. 63, p. 2759-2764.*
Don M M et al: "Kinetics of hyaluronic acid production by *Streptococcus zooepidemicus* considering the effect of glucose", Biochemical Engineering Journal, Elsevier, Amsterdam, NL, vol. 49, No. 1, Mar. 15, 2010, pp. 95-103.
Jong-Hyuk IM et al: "Optimization of medium components for high-molecular-weight hyaluronic acid production by *Streptococcus* sp. ID9102 via a statistical approach", Journal of Industrial Microbiology & Biotechnology; Official Journal of the Society for Industrial Microbiology, Springer, Berlin, DE, vol. 36, No. 11, 22 Jul. 2009, pp. 1337-1344.
Liu L et al: "Enhanced hyaluronic acid production by a two-stage culture strategy based on the modeling of batch and fed-batch cultivation of *Streptococcus zooepidemicus*", Bioresource Technology, Elsevier BV, GB, vol. 99, No. 17. Nov. 1, 2008, pp. 8532-8536.
European Search Report dated May 31, 2012, issued in corresponding European Patent Application No. 08791671.4—1521 / 2311971 PCT/JP2008063427.

* cited by examiner

*Primary Examiner* — Taeyoon Kim
*Assistant Examiner* — Tiffany Gough
(74) *Attorney, Agent, or Firm* — Stein IP, LLC

(57) ABSTRACT

It is intended to provide a simple method for producing hyaluronic acid at a high yield. Further, it is also intended to provide a method for producing hyaluronic acid in a short period of time. The invention provides a method for producing hyaluronic acid including a step of culturing a microorganism having the capability to produce hyaluronic acid and a step of adding glutamine and arginine to a culture medium during late logarithmic growth phase of the microorganism.

6 Claims, 2 Drawing Sheets

METHOD FOR PRODUCING HYALURONIC ACID

TECHNICAL FIELD

The present invention relates to a method for producing hyaluronic acid using a microorganism.

BACKGROUND ART

Hyaluronic acid has been used as a moisturizing agent in cosmetics as well as a drug in ophthalmology, orthopedic surgery and dermatology etc. While hyaluronic acid can be produced from extracts of animal tissues, such as cock's comb and the vitreous body of cattle eyes, contaminants such as chondroitin sulfate be mixed in and hyaluronidases present in tissues can easily break down hyaluronic acid into low molecular weight substances, so hyaluronic acid has also been produced from culture media obtained by culturing microorganisms capable of producing hyaluronic acid (fermentation process) (Patent Document 1). Compared to the extraction process, the fermentation process allows hyaluronic acid to be produced from a fixed raw material using a fixed method, which keeps the quality of the product at a certain level, and therefore has greater industrial utility.

Further, in order to produce hyaluronic acid industrially, fermentation processes in which various culture medium components are used for fermentation have been developed (Patent Documents 2 to 4). Patent Document 2 describes a fermentation process in which a culture medium with increased amounts of eight types of amino acids generally considered to be necessary for growth is used as the effective component in hyaluronic acid production. Additionally, Patent Document 3 describes a fermentation process in which a culture medium with increased amounts of arginine and/or glutamic acid is used. Additionally, Patent Document 4 describes a fermentation process in which a culture medium with an increased amount of arginine is used.

Patent Document 1: JP-B H4-12960
Patent Document 2: JP-A H7-46992
Patent Document 3: JP-A S62-289198
Patent Document 4: JP-A S63-141594

DISCLOSURE OF THE INVENTION

Problems to be Solved by the Invention

However, most of the conventional culture media considered to be suitable for culturing contain a large number of components, the preparation of the culture media is complex, and the procedure for isolation and purification of hyaluronic acid from the culture media is complicated, so there has been a demand for further improvements of these industrial production methods. Additionally, with regard to other conventional methods, there has also been a demand for their further improvement as industrial production methods.

The present invention was achieved in view of the above issues, and the object is to provide a simple method for producing hyaluronic acid at a high yield. Another object is to provide a method for producing hyaluronic acid in a short period of time.

Means for Solving the Problems

In order to achieve the above objects, the present inventors performed diligent research and found as a result that the production of hyaluronic acid can be improved by adding a combination of arginine and glutamine to the culture medium during a specific phase of culture, and so the present invention was completed.

In other words, the present invention provides a method for producing hyaluronic acid comprising a step of culturing a microorganism having the capability of producing hyaluronic acid, and a step of adding glutamine and arginine to the culture medium during late logarithmic growth phase of the microorganism. According to this production method, it is possible to produce hyaluronic acid easily at a high yield in a short period of time by adding a combination of glutamine and arginine to the culture medium during a specific phase of culture.

Effects of the Invention

According to the method for producing hyaluronic acid of the present invention, it is possible to produce hyaluronic acid easily at a high yield in a short period of time by adding a combination of glutamine and arginine to the culture medium during a specific phase of culture of a microorganism having the capability of producing hyaluronic acid.

MODES FOR CARRYING OUT THE INVENTION

[Explanation of Terminology]

Figure 1:
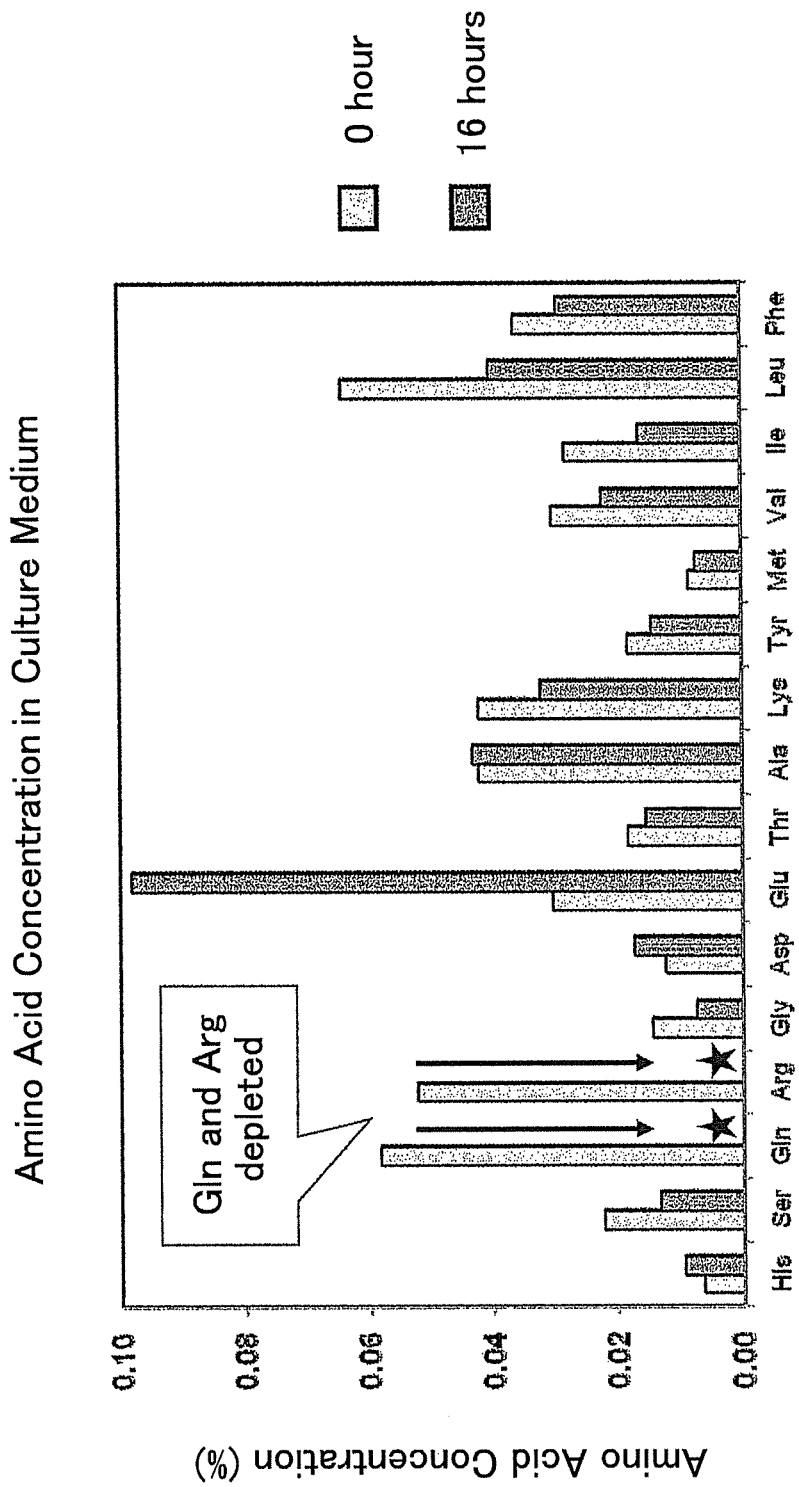
FIG. 1 is a graph of the amino acid concentration in the culture medium when culturing a microorganism that produces hyaluronic acid.

In the present specification, "late logarithmic growth phase" shall refer to the period from the later half of the logarithmic growth phase to the quiescent phase (stationary phase) in which a microorganism is in a state of sufficient growth. Additionally, the logarithmic growth phase shall refer to a phase in microorganism culture in which the microorganism grows by binary fission in a fixed period of time and the logarithm of the number of cells is a straight line with respect to time. The late logarithmic growth phase can be determined using arbitrary indicators and methods known to those skilled in the art. For example, turbidity or specific growth rate may be used as indicators for the sake of simplicity, though the present method is not limited thereto.

In the present specification, "turbidity" shall refer to the most common, simple and rapid measuring method in which the growth of a microorganism is determined by the cloudiness of the culture medium (amount of bacteria in the culture medium). Light is shone on the culture medium and the amount of light blocked by scattering and absorption is determined. Since the microorganism producing hyaluronic acid is a fine particle, the number of microorganisms and the turbidity of the culture medium have a proportional relationship. For example, turbidity may be determined as follows.

Light of a single wavelength at 660 nm is shone on a culture medium, and the transmitted light is measured by a spectrophotometer. Here, the intensities of the incident light and the transmitted light are respectively referred to as $I_0$ and I, the thickness of the light-transmitting layer as L and the absorbance as τ, and the absorbance obtained by the following formula is defined as the turbidity (OD) of the culture medium.

$$I=I_0 Exp(-\tau L)$$ [Formula 1]

Additionally, when the medium prior to culture has a non-negligible turbidity, the turbidity of a control medium may be subtracted from the turbidity of the culture medium.

In the present specification, the late logarithmic growth phase may be used to indicate a phase in which the culture medium exhibits a turbidity of at least 0.5 at 660 nm. Additionally, the above phase of logarithmic growth is preferably a phase exhibiting a turbidity of at least 1.0, more preferably a phase exhibiting a turbidity of at least 2.0 and even more preferably a phase exhibiting a turbidity of at least 3.0.

In the present specification, "specific growth rate" shall refer to a value defined by the following formula.

$$\text{Specific growth rate } (h^{-1})=\ln 2/\text{generation time of bacteria (h)}$$ [Formula 2]

Here, the generation time of bacteria refers to the time required for the microorganism producing hyaluronic acid to double. When the microorganism producing hyaluronic acid has sufficiently grown, the growth rate decreases due to nutrient depletion and metabolite accumulation etc., causing the specific growth rate to also decrease.

In the present specification, the late logarithmic growth phase may be used to indicate a phase exhibiting a specific growth rate of at most $0.5\ h^{-1}$. Additionally, the above phase of logarithmic growth is preferably a phase exhibiting a specific growth rate of at most $0.4\ h^{-1}$, more preferably a phase exhibiting a specific growth rate of at most $0.3\ h^{-1}$, even more preferably a phase exhibiting a specific growth rate of most $0.2\ h^{-1}$ and further preferably a phase exhibiting a specific growth rate of at most $0.1\ h^{-1}$. Additionally, though obvious, the specific growth rate is greater than $0\ h^{-1}$.

In the present specification, "*Streptococcus* bacterium" includes arbitrary bacteria belonging to the genus *Streptococcus* and mutant strains thereof capable of producing hyaluronic acid, and examples may include, but are not limited to, *Streptococcus equi*, *Streptococcus zooepidemicus*, *Streptococcus equisimilis*, *Streptococcus dysgalactiae*, *Streptococcus pyogenes* and mutant strains thereof.

In the present specification, the definitions of chemical substances such as "glutamine", "arginine" and "hyaluronic acid", unless specifically indicated otherwise, shall include arbitrary salts usable within a range not compromising the object of the invention (examples may include, but are not limited to, metal salts such as sodium salts and potassium salts, and acid adducts such as hydrochloride salts, phosphate salts and citrate salts) and hydrates as well as mixtures thereof.

Additionally, with regard to each numerical range in the present specification, the expression "to" shall include both the upper limit and the lower limit.

Embodiments

Herebelow, embodiments for carrying out the present invention shall be explained.

One embodiment of the present invention is a method for producing hyaluronic acid comprising a step of culturing a microorganism having the capability of producing hyaluronic acid, and a step of adding glutamine and arginine to the culture medium during late logarithmic growth phase of the microorganism. According to this production method, the addition of both arginine and glutamine during a later phase of the culture allows the growth inhibitory effect of arginine at a high concentration on microorganisms to be suppressed, so hyaluronic acid can be produced at a high yield in a short period of time. Additionally, in the present embodiment, the addition of glutamine and arginine after the start of culture allows a regular medium to be used without the need to prepare a medium that requires particularly complex preparation. Further, by not adding any unnecessary nutrient components, the amount of work required for the step of isolating and purifying hyaluronic acid is reduced, allowing quality to be maintained and productivity to be stabilized.

A commonly used culture method can be used as the culture method used in the above embodiment. In other words, for example, a carbon source consisting of a sugar moiety such as glucose, fructose, galactose or sucrose; an inorganic salt such as potassium primary phosphate, potassium secondary phosphate, magnesium nitrate, sodium sulfite, sodium thiosulfate or ammonium phosphate; an organic nutrient source such as polypeptone, casamino acid, yeast extract, corn steep liquor or liquid soy hydrolysate; and various vitamins, if necessary, can be favorably used for the medium. The culture can be carried out using a known method, for example, an aerobic culture method such as aeration-agitation culture. The culture temperature is preferably, but not limited to, 30 to 35° C. Since the pH of the culture medium decreases with the growth of the microorganism, a pH adjuster such as sodium hydroxide, potassium hydroxide or ammonia, for example, may be added to control the pH so that it is 7.0 to 9.0.

Glutamine and arginine may be added simultaneously or separately, and they may be added with other components such as a buffer or a salt in a range not compromising the object of the present invention; however, when considering the subsequent isolation and purification step, it is preferred that there be fewer components requiring purification. For example, nutrient components or active components other than glutamine and arginine are preferably at most 0.001% and more preferably at most 0.0005% or not present.

Additionally, a further embodiment of the present invention is the above production method in which the above late logarithmic growth phase is a phase in which the culture medium exhibits a turbidity of at least 0.5 at 660 nm. The addition of glutamine and arginine during a phase exhibiting a turbidity of at least 0.5 more certainly improves the yield of hyaluronic acid. Glutamine and arginine are more preferably added during a phase in which the above turbidity is at least 2.0. By adding glutamine and arginine during a phase exhibiting the above turbidity indicating that the microorganism is in a state of sufficient growth, it is possible to obtain an even higher yield of hyaluronic acid. Glutamine and arginine are further preferably added during a phase in which the above turbidity is at least 3.0, as doing so allows improvement in the yield to be achieved certainly within a short period of time.

Additionally, with regard to turbidity, while the turbidity of a culture medium can be used as is, when the turbidity of a control medium, such as a medium prior to culture, is non-negligibly high (for example, but not limited to, at least 0.01 or 0.05), the turbidity obtained by subtracting the turbidity of the control medium from that of the culture medium may be used as the indicator. A medium prior to culture or a medium not inoculated with a microorganism may be used as the control medium.

In addition, the above turbidity-defined phase for addition is an example of how a range of the phase can be specifically determined by an indicator, and it is not always necessary to perform the step of determining turbidity under the above conditions. Therefore, though obvious, even if turbidity were measured and determined at 600 nm, it would still be understood as being covered by the above embodiment as long as the turbidity at 660 nm is covered by the scope of the above embodiment.

Additionally, another further embodiment of the present invention is the above production method in which the above late logarithmic growth phase is a phase exhibiting a specific growth rate of at most $0.5\ h^{-1}$. The addition of glutamine and arginine during a phase exhibiting a specific growth rate of at most $0.5\ h^{-1}$ more certainly improves the yield of hyaluronic acid. Glutamine and arginine are more preferably added during a phase exhibiting a specific growth rate of at most $0.4\ h^{-1}$. By adding glutamine and arginine during a phase exhibiting the above specific growth rate indicating that the microorganism is in a state of sufficient growth, it is possible to obtain an even higher yield of hyaluronic acid. Glutamine and arginine are further preferably added during a phase exhibiting a specific growth rate of at most $0.3\ h^{-1}$, as doing so allows improvement in the yield to be achieved certainly within a short period of time.

In addition, the above specific growth rate-defined phase for addition is an example of how a range of the phase can be specifically determined using an indicator, and it is not always necessary to perform the step of determining specific growth rate under the above conditions.

Additionally, a further embodiment of the present invention is the above production method in which the above microorganism having the capability of producing hyaluronic acid is a *Streptococcus* bacterium. The use of a commonly used *Streptococcus* bacterium having the capability of producing hyaluronic acid allows for simple and certain industrial production of hyaluronic acid. The *Streptococcus* bacterium used here includes *Streptococcus* bacteria isolated from nature and mutant strains thereof.

Further, *Streptococcus equi*, *Streptococcus equi* mutant strain FM-100 (Fermentation Research Institute, the Agency of Industrial Science and Technology, Deposit No. 9027) or *Streptococcus equi* mutant strain FM-300 (Fermentation Research Institute, the Agency of Industrial Science and Technology, Deposit No. 2319) may be favorably used as the *Streptococcus* bacterium in the above embodiment. By using these strains that stably produce hyaluronic acid at a high yield, it is possible to produce hyaluronic acid at a higher yield and at a more stable productivity.

Additionally, while the amount of glutamine added in the above embodiment is not particularly limited as long as it is within a range not compromising the object of the present invention, an excess amount would reduce the extent of the effects, so the amount is preferably 0.01 to 0.3% and more preferably at least 0.05%, at least 0.1% and/or at most 0.2%. By using glutamine within this concentration range, the yield can be improved more certainly and a production stabilizing effect can be achieved. Additionally, by using an amount of glutamine equal to or less than the above upper limit, the amount of work required for the subsequent isolation and purification step can be reduced.

Additionally, while the amount of arginine added in the above embodiment is not particularly limited as long as it is within a range not compromising the object of the present invention, an excess amount would reduce the extent of the effects, so the amount is preferably 0.01 to 0.2% and more preferably at least 0.05%, at least 0.1% and/or at most 0.1%. By using arginine within this concentration range, the yield can be improved more certainly and a production stabilizing effect can be achieved. Additionally, by using an amount of arginine equal to or less than the above upper limit, the amount of work required for the subsequent isolation and purification step can be reduced, and the growth inhibitory effect of arginine can also be more strongly prevented.

In addition, the present invention is not limited to the production methods explained in the above embodiments, which are disclosed for the purpose of illustration. The technical scope of the present invention is defined by the recitations of the claims, and it is possible for those skilled in the art to make various design changes to the technical scope of the invention recited in the claims.

For example, the above production method may contain another further step, or another further step or method may be carried out following the above production method. Examples of such a step or method include a sterilization step by activated charcoal or filtration, a neutralization step or crystallization step, and a step for purifying and removing contaminants, such as endotoxins, proteins, nucleic acids and metals by chromatography or centrifugation.

EXAMPLES

Herebelow, the present invention shall be further explained using examples, though the present invention is not limited thereto.

First, a brief summary of the preliminary experiments relating to the present invention is indicated herebelow. These preliminary experiment examples were examined under the same conditions within the same preliminary experiments using culture conditions similar to those of Example 1 described below. Additionally, in each experimental graph, hyaluronic acid is denoted as "HA", glutamine as "Gln", arginine as "Arg", addition of components to the medium from the start of culture as "en bloc addition", addition of components to the medium after the start of culture (especially during late logarithmic growth phase) as "later addition". Additionally, for some of the experiment examples, the amount of hyaluronic acid produced was evaluated using viscosity, which correlates with hyaluronic acid concentration, as an indicator.

Preliminary Experiment 1

Changes in the concentration of various amino acids during culture of microorganisms producing hyaluronic acid under conventional standard conditions were examined. The results are shown in the graph of FIG. 1. While the various amino acids, depending on the type, showed either the behavior of a reduction, remaining constant or an increase in the course of culture, the amounts of glutamine and arginine were observed to decrease drastically, so under standard culture conditions, their depletion was observed.

Preliminary Experiment 2

Based on the results of Preliminary Experiment 1, further studies were carried out with addition of glutamine and arginine in mind. Although the mechanism of arginine in the cell is unclear, it alone has been reported to inhibit growth without improving hyaluronic acid yield. With respect to this issue, studies were carried out in consideration of further improvements based on improving the method for adding arginine.

Figure 2:
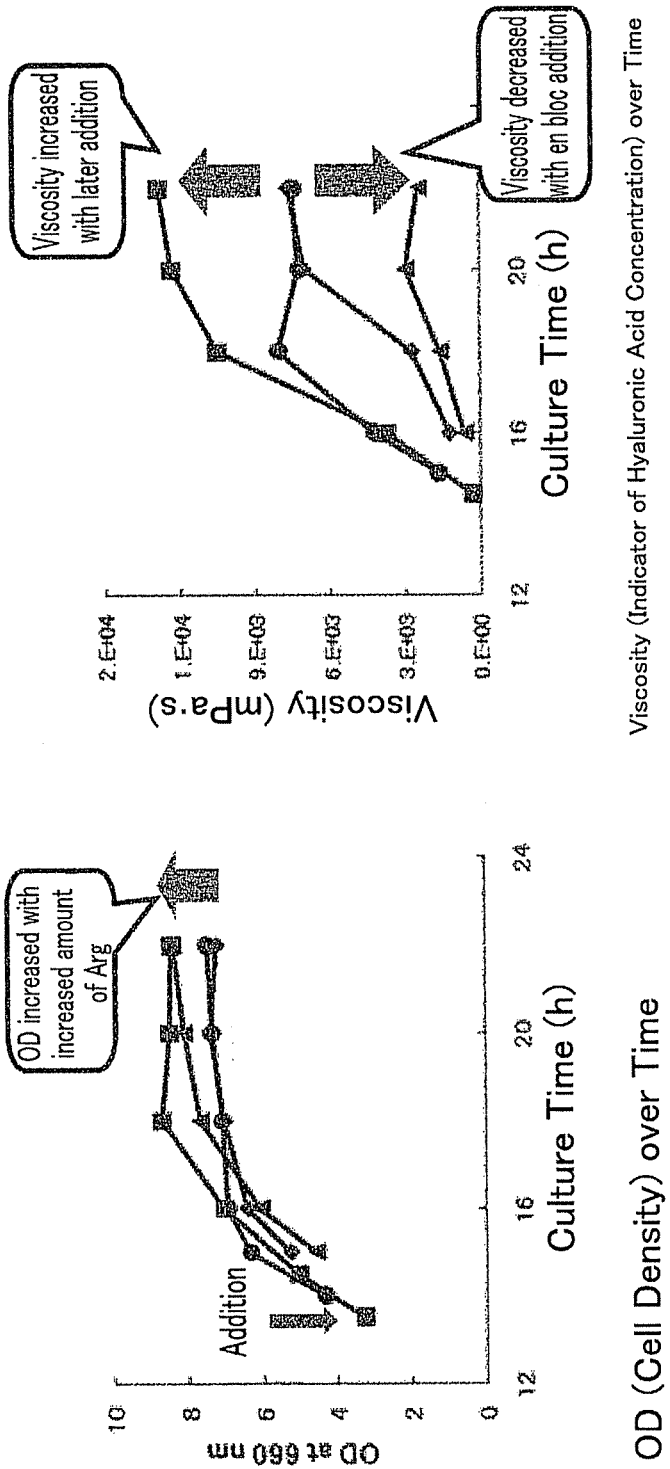
FIG. 2 shows graphs comparing situations where arginine was added en bloc or added later. The graph on the left shows cell density over time and the graph on the right shows viscosity (indicator of hyaluronic acid concentration) over time.

As a result thereof, as shown in the graph in FIG. 2, the addition of arginine later, not en bloc, during culture was found to dramatically increase the hyaluronic acid concentration (in the graph, the hyaluronic acid concentration is evaluated by viscosity). These experimental results on arginine may be summarized by the table below.

TABLE 1

| Addition Method | Cell Growth | | Viscosity |
| --- | --- | --- | --- |
| | Amount of Cells | Culture Time | |
| En bloc addition | High | Late | Low |
| Later addition | High | No change | High |

Preliminary Experiment 3

Based on the findings from the above experimental results, experiments were performed under standard conditions with glutamine and arginine added later during culture of the microorganism producing hyaluronic acid. The experimental results are shown in Table 2 below.

TABLE 2

Combination of Gln and Arg Dramatically Increased Hyaluronic Acid (HA) Yield

| | Addition Condition | | Value Reached | | |
| --- | --- | --- | --- | --- | --- |
| Condition | Gln (%) | Arg Later Addition (%) | OD | HA Concentration (%) | Increase in HA Yield (%) |
| Standard Condition | 0.06 | — | 7.3 | 0.41 | — |
| Gln Increased | 0.15 | — | 7.7 | 0.51 | 24 |
| Arg Later Addition | 0.06 | 0.05 | 8.7 | 0.43 | 5 |
| Gln Increased + Arg Later Addition | 0.16 | 0.05 | 8.2 | 0.58 | 41 |
| Gln + Arg Later Addition | 0.06 + 0.1 | 0.05 | 8.5 | 0.62 | 51 |

As shown in Table 2, the amount of hyaluronic acid produced was observed to be greatly increased by the later addition of the glutamine and arginine combination.

Comparative Experiment Example 1

The experiments for Examples 1 to 4 and Comparative Examples 1 to 4 described below were carried out under the same conditions as Example 1, and the hyaluronic acid concentration and the time taken to reach a certain hyaluronic acid concentration (evaluated using viscosity) were measured. The results are shown in Table 3.

TABLE 3

Evaluation Results of Effects on Increased Gln and Arg Addition

| Culture Condition | | | Value (Maximum) Reached | | | Time Taken to Reach Stationary Phase | |
| --- | --- | --- | --- | --- | --- | --- | --- |
| Gln | Arg | Time Added | OD | Viscosity (mPa · s) | HA Concentration (%) | OD | Viscosity |
| 0.06% | — | — | 7.3 | 8618 | 0.41 | 20 | 20 |
| 0.1% | 0.05% later addition | After 13 hours | 8.1 | 17621 | 0.57 | 16 | 18 (22) |
| 0.16% | 0.05% later addition | After 13.5 hours | 8.2 | 18176 | 0.58 | 17 | 18 (22) |
| 0.06 + 0.1% later addition | 0.05% later addition | After 13.5 hours | 8.5 | At least 21000 | 0.62 | 16 | 18 (22) |
| 0.06 + 0.1% later addition | 0.1% later addition | After 14 hours | 9.1 | 18346 | 0.60 | 16 | 18 (24) |
| 0.1 + 0.1% later addition | 0.05% later addition | After 14.3 hours | 8.2 | 19840 | 0.55 | 18 | 18 (24) |

Time taken to reach stationary phase: time taken for OD to reach at least 6.8, for viscosity to reach at least 7000 mPa · s;
( ) is the time taken to reach maximum viscosity
* The amount of glutamine in the table represents the amount added during culture.

Example 1

The conditions for the initial stage of culture were achieved by heat sterilizing 1 liter of a medium consisting of 1.5% polypeptone and 0.5% yeast extract, then adding glucose, dipotassium hydrogen phosphate and glutamine so as to reach 6%, 0.1% and 0.06% respectively, *Streptococcus equi* FM-100 (Fermentation Research Institute, the Agency of Industrial Science and Technology, Deposit No. 9027) were then inoculated, and culture was started at an agitation of 500 rpm, a temperature of 33° C. and pH 8.0 (controlled by automatic dripping of 25% sodium hydroxide) while air was circulated at 1 vvm. The culture medium was collected over time, and amounts equivalent to 0.1% glutamine and 0.05% arginine were added when the culture medium reached a turbidity of 3.6 at 660 nm and a specific growth rate of 0.34 $h^{-1}$. Culture was continued until the viscosity of the culture medium stopped increasing due to accumulation of hyaluronic acid. After the viscosity of the culture medium stopped increasing, the culture medium was adjusted to pH 3 using nitric acid, cells were removed by centrifugation and the supernatant was collected.

In order to determine the amount of hyaluronic acid in the medium, the supernatant was sequentially diluted and the hyaluronic acid concentration in the medium was measured by size exclusion chromatography equipped with a differential refractometer. A high yield of 6.2 g/L of hyaluronic acid in the medium was obtained and the culture time taken to reach a hyaluronic acid concentration of 4.0 g/L was a short period of time of 17 hours.

Example 2

Culture was started in the same manner as Example 1, and amounts equivalent to 0.1% glutamine and 0.1% arginine were added. A high yield of 6.0 g/L of hyaluronic acid in the medium was obtained, and the culture time taken to reach a hyaluronic acid concentration of 4.0 g/L was a short period of time of 17 hours.

Example 3

Culture was started in the same manner as Example 1, glutamine was added at an amount equivalent to 0.04%, which was less than that in Example 1 and arginine was added at an amount equivalent to 0.05%. The addition was performed during a phase in which the cell density was an OD of 5.3 and the specific growth rate was 0.16. Since the amount of glutamine added was less, a high yield of 5.2 g/L, which was less than those in Examples 1 and 2, of hyaluronic acid in the medium was obtained, and the culture time taken to reach a hyaluronic acid concentration of 4.0 g/L was a short period of time of 18 hours.

Example 4

Culture was started in the same manner as Example 3, and glutamine and arginine were added in the same manner as Example 3. The addition was performed during a phase in which the cell density was an OD of 7.0 and the specific growth rate was 0.05. A high yield of 5.0 g/L of hyaluronic acid in the medium was obtained, and the culture time taken to reach a hyaluronic acid concentration of 4.0 g/L was a short period of time of 18 hours.

Comparative Example 1

Culture was started in the same manner as Example 1, and glutamine and arginine were not added. The hyaluronic acid in the medium was a low yield of 4.1 g/L and the culture time taken to reach a hyaluronic acid concentration of 4.0 g/L was a long period of time of 23 hours.

Comparative Example 2

Culture was started in the same manner as Example 1, and only 0.05% arginine was added. While the culture time taken to reach a hyaluronic acid of 4.0 g/L was 18 hours, the hyaluronic acid in the medium was a low yield of 4.3 g/L.

Comparative Example 3

Culture was started in the same manner as Example 1, and only 0.1% glutamine was added. The hyaluronic acid in the medium was a low yield of 5.3 g/L. The culture time taken to reach a hyaluronic acid of 4.0 g/L was a long period of time of 21 hours.

Comparative Example 4

Culture was started in the same manner as Example 3, and glutamine and arginine were added in the same manner as Example 3. The addition was performed during a phase in which the cell density was an OD of 0.0001 and the specific growth rate was 1.0. The hyaluronic acid in the medium was a low yield of 4.0 g/L.

Comparative Experiment Example 2

Further comparative experiments were carried out using the same methods as the above Examples 1 to 4 and Comparative Examples 1 to 4 (glucose concentration was 6%). The results are shown in Table 4 below. These comparative experiments also confirmed that the amount of hyaluronic acid produced (HA concentration in the table) increased when glutamine and arginine were added to the culture media during late logarithmic growth phase.

TABLE 4

| | Concentration of Amino Acid Added (%) | | Phase when Amino Acid was Added | | HA Concentration in medium | Time Taken to Reach approximately 4.0 g/L HA |
| --- | --- | --- | --- | --- | --- | --- |
| | | | Cell Density | Specific Growth Rate | | |
| | Gln | Arg | (OD660) | ($h^{-1}$) | (g/L) | Concentration (hr) |
| Example 1 | 0.1 | 0.05 | 3.6 | 0.34 | 6.2 | 17 |
| Example 2 | 0.1 | 0.1 | 4.8 | 0.41 | 6 | 17 |
| Example 3 | 0.04 | 0.05 | 5.3 | 0.16 | 5.2 | 18 |
| Example 4 | 0.04 | 0.05 | 7 | 0.05 | 5 | 18 |
| Comparative Example 1 | — | — | — | — | 4.1 | 23 |
| Comparative Example 2 | — | 0.05 | 5 | 0.31 | 4.3 | 18 |
| Comparative Example 3 | 0.1 | — | 0.0001 | 1 | 5.3 | 21 |
| Comparative Example 4 | 0.04 | 0.05 | 0.0001 | 1 | 4.0 | 20 |

* The amount of glutamine in the Table represents the amount added during culture.

SUMMARY

The above experiments confirmed that it is possible to produce hyaluronic acid at a high yield in a short period of time using the method of adding glutamine and arginine to a culture medium during late logarithmic growth phase, as compared to conventional art.

The present invention has been explained on the basis of examples above. These examples are only for the purpose of illustration, and those skilled in the art will understand that various modifications are possible, and that such modifications are also covered by the scope of the present invention.

The invention claimed is:

1. A method for producing hyaluronic acid comprising culturing a microorganism having the capability of producing hyaluronic acid in a culture medium wherein said microorganism is *Streptococcus equi, Streptococcus equi* mutant strain FM-100 (Fermentation Research Institute, the Agency of Industrial Science and Technology, Deposit No. 9027) or *Streptococcus equi* mutant strain FM-300 (Fermentation Research Institute, the Agency of Industrial Science and Technology, Deposit No. 2319), adding glutamine and arginine to the culture medium during late logarithmic growth phase of the microorganism and producing hyaluronic acid.

2. The method of claim 1, wherein said late logarithmic growth phase is a phase in which the culture medium exhibits a turbidity of at least 0.5 at 660 nm.

3. The method of claim 1, wherein said late logarithmic growth phase is a phase in which the culture medium exhibits a turbidity of at least 2.0 at 660 nm.

4. The method of claim 1, wherein said late logarithmic growth phase is a phase exhibiting a specific growth rate of at most $0.5\ h^{-1}$.

5. The method of claim 1, wherein the concentration of said glutamine is 0.01 to 0.3%.

6. The method of claim 1, wherein the concentration of said arginine is 0.01 to 0.2%.

* * * * *